US005700268A

United States Patent [19]
Bertin

[11] Patent Number: 5,700,268
[45] Date of Patent: Dec. 23, 1997

[54] DEVICE FOR MEASURING LEG LENGTH AND OFF-SET FOR A TOTAL HIP REPLACEMENT

[75] Inventor: Kim C. Bertin, Salt Lake City, Utah

[73] Assignee: Zimmer, Inc., Warsaw, Ind.

[21] Appl. No.: 778,848

[22] Filed: Jan. 6, 1997

[51] Int. Cl.⁶ .................................................. A61B 17/56
[52] U.S. Cl. .................................................. 606/102
[58] Field of Search .................. 606/102, 88, 89, 606/86, 96, 99, 100; 128/774, 782; 33/511, 512, 515

[56] References Cited

U.S. PATENT DOCUMENTS

| | | |
|---|---|---|
| 5,122,145 | 6/1992 | Fishbane. |
| 5,318,571 | 6/1994 | Benson. |
| 5,423,828 | 6/1995 | Benson. |
| 5,435,321 | 7/1995 | McMillen et al.. |
| 5,490,518 | 2/1996 | Russo et al.. |
| 5,603,717 | 2/1997 | Benson ................................. 606/102 |
| 5,616,147 | 4/1997 | Gadelius ............................... 606/102 |

FOREIGN PATENT DOCUMENTS

| 2684287 | 6/1993 | France. |
| WO9412109 | 5/1994 | WIPO. |

OTHER PUBLICATIONS

Zimmer, Inc. Brochure "Hip General Instruments" p. A129.
Centralign Precoat Hip Prosthesis Surgical Technique brochure, Zimmer, Inc. pp. 5 through 7.

*Primary Examiner*—Guy V. Tucker
*Attorney, Agent, or Firm*—M. Reid Russell

[57] ABSTRACT

A device for use in an orthopedic surgical procedure for replacement of a patient's hip that, prior to dislocation of the pathologic hip, is used by the surgeon to determine leg length and leg displacement, with these measurements then used as references for reproducing or adjusting leg length and positioning. The device includes an ilium pin that is to be driven into the patient's ilium to serve as a fixed reference. Preferably, the ilium pin includes a pair of pointed end portions, the one forking off from the other, with the ilium pin top end arranged to be driven into the ilium using a driver. A straight measuring bar that includes an ilium mounting end is arranged for fitting onto the ilium pin to extend at a right angle therefrom and a scale is formed around the opening through the ilium mounting end and a radial indicator is scribed into the top of the ilium pin, for use in determining femur medial or lateral displacement. The measuring bar includes a scale scribed therealong and is arranged to receive a femoral slide fitted to slid over the scale, whereby a femoral slide side is to serve as an indicator for comparison to the scale markings for determining femoral slide positioning from the ilium pin. The femoral slide further includes a hole formed therethrough that a straight femoral pin is fitted through, forming a right angle to the measuring bar, the femoral pin having, has a pointed end to contact a fixed location on the proximal femur. A scale is scribed along a femoral pin upper portion that is arranged to receive an indicator sleeve fitted to travel along the femoral pin to engage a top surface of the femoral slide for comparison with the scale markings to determine a distance the femoral pin end is extended from the femoral slide. The device includes set screw type locks for releasably locking the device components together allowing them to be maintained in position and then reinstalled to the ilium after installation of the hip prosthesis for use in duplicating or adjusting the leg positioning relative to the acetabulum, as the surgeon determines.

11 Claims, 5 Drawing Sheets

DEVICE FOR MEASURING LEG LENGTH AND OFF-SET FOR A TOTAL HIP REPLACEMENT

BACKGROUND OF THE INVENTION

1. Field of the Invention

This invention relates to devices for measuring leg length and hip displacement during a total hip replacement procedure.

2. Prior Art

Generally, in a total hip replacement surgical procedure, an accurate reproduction of the length of the leg undergoing the procedure has largely depended upon the skill of the surgeon who, in a commonly used procedure, compares the patient's leg under repair with their other leg to estimate prosthesis selection and seating. Alternatively, where the original length of the leg undergoing the procedure is to be reproduced, a pin, such as a Steinmann pin, is seated in the hip to extend at approximately a right angle therefrom. Then, a straight device, such as a ruler, or the like, is positioned at approximately a right angle across the pin, as with a use of a level, to span the joint. Thereafter, a second pin is held against and at a right angle to the straight device, and a mark is placed at a point on the proximal femur that is past where the bone will be resectioned. The distance between the approximately parallel vertical pins is then measured. The surgeon then attempts to reproduce this measured distance by a prosthesis selection and femoral member seating.

A number of devices and procedures that have utilized like arrangements to the above set out pins, a ruler, and a level have been practiced, and an example of a device and its use that utilizes this procedure is shown in a U.S. Pat. No. 5,318,571 to Benson, with like devices and their use shown in a PCT Application identified as WO94/12109 to Gadeluis and in a French Patent No. 2,684,287 to Chagneau, et. al. Additionally, surgical tooling and systems for their use to, prior to the surgical procedure, determine leg length to be reproduced by a prosthesis selection and mounting, are well known and currently in use. For example, Zimmer U.S.A. markets a system known as a "Harris Leg Length Caliper Set" for use in patient leg length reproduction. While such devices and their use have provided a surgeon with a good approximation of the patient's leg length and have facilitated its reproduction, the success of such surgical procedure is still largely dependent upon the surgeon's abilities. A recent U.S. Pat. No. 5,122,145 to Fishbane improves upon such earlier devices and procedures. The Fishbane patent utilizes a pair of pins that are mounted side by side in the ilium to be approximately parallel to one another. This pair of pins receives a bar seated thereon wherefrom a pivot mounted measuring device extends. This pivot mounted measuring device is a section formed to extend well over the joint and includes a right angle barrel member that receives a pin fitted therethrough to extend to a femoral location beyond the joint. A bubble level is positioned on the straight section, for use in leveling that section, with the distance between the ilium pins and femur pin then measured as with a ruler. A use of the Fishbane device produces a more accurate leg length measurement across the joint to a fixed point, and for reproducing that measurement in the leg whereon the surgical procedure is practiced upon, than was possible with earlier devices and systems. Such accurate measure allows a surgeon to use the original leg length measurement as a base against which to increase or decrease the repaired leg length, with such leg length reproduction or adjustment accomplished by the prosthesis selection and its mounting.

The present invention, like the device of the Fishbane patent, utilizes a pin device that is for seating, at a right angle, in the ilium with a straight measuring bar member for coupling, at one end, to the pin device to extend at a right angle therefrom. A movable femoral pin slide is arranged to travel along and can be locked in place to the measuring bar member and includes a pin barrel extending therefrom. The pin barrel forms a right angle to the measuring bar member and is to accommodate a femoral pin fitted therethrough, such that an end of the pin will contact a mark scribed on the femur. Thereafter, by an inspection of the femoral pin slide position along a scale scribed on the measuring bar, the distance between the ilium pin device and the mark scribed on the femur. Additionally, the present invention provides a capability for measuring an off set of the femur to the acetabulum where the ilium pin device serves as a measuring reference. Accordingly, the invention allows a surgeon in a hip replacement procedure to reproduce the patient's original leg length or to shorten or lengthen that patient's leg length and further is used for determining to reproduce the angle of off-set of the femur medially or laterally to the acetabulum, optimizing a ball and socket seating of the prosthetic femoral ball end in the acetabular member so as to minimize a likelihood of dislocation.

SUMMARY OF THE INVENTION

It is a principal object of the present invention to provide a measuring device for use in a total hip replacement procedure for establishing a distance between a straight pin device fixed in the ilium, above the acetabulum or socket, and a location on a proximal femur, below the femoral head, and for determining a measurement of medial and lateral displacement of the femur relative to the acetabulum prior to dislocation of the pathologic hip.

Another object of the present invention is to provide a measuring device that, after insertion of a hip prosthesis, can be refitted between the straight pin device fixed in the ilium, above the acetabulum, and to the fixed location along the proximal femur to ascertain whether the measurements taken before the surgery have been accurately reproduced, or whether adjustments are needed to reproduce or to adjust leg length and off-set prior to closure.

Another object of the present invention is to provide a measuring device that is used to establish base line measurements for use by the surgeon in making changes or adjustments to a patient's leg length and off-set in a hip replacement procedure as for example, a leg lengthening or shortening, and/or a change in medial or lateral displacement, or the like.

Another object of the present invention is to provide a measuring device that incorporates a double ended pin device that is for driving, using an appropriate driver, into the ilium to form approximately a right angle, with the pin device to remain in the ilium during the surgical procedure and is to receive and maintain a horizontal measuring bar fitted at a right angle thereto that includes a scale for use in measuring a distance from the pin device to a femoral slide positioned at a location along the measuring bar wherefrom a femoral pin is extended to where a pointed femoral pin end engages the fixed location on the proximal femur.

Still another object of the present invention is to provide a measuring device for determining, prior to a dislocation of the pathologic hip, femur medial or lateral displacement to the acetabulum by a comparison of a straight radial line formed in a top end of the double ended pin to a degree mark on a scale representing a full circle that is scribed around opening through the horizontal measuring bar ilium pin mount end wherethrough the double end pin top end is fitted.

Still another object of the present invention is to provide a measuring device that is simple and reliable for use by a surgeon in a total hip replacement surgical procedure.

Principal features of the present invention in a measuring device for use in a total hip replacement procedure for measuring leg length and off-set that includes a single ilium pin having a straight shaft upper body and branches below a mid-section into a double pin lower end portion. The double pin ends are pointed for driving, utilizing a driver of the invention, into a patient's ilium, above the acetabulum or socket. The ilium pin is formed with a flat top face that has a radial marking scribed thereon at a right angle to an imaginary straight line between the ilium pin double pin end. The ilium pin top end is to fit into a hole formed through an ilium end mount of a straight measuring bar to align with a marking of a scale in degrees of a full circle that is formed around the ilium end mount hole that the ilium pin top end is fitted through. The alignment of the ilium pin radial marking with a scale marking to establish an initial medial or lateral off-set of the patient's femur relative to the patient's acetabulum or socket and is taken prior to a dislocation of the pathologic hip in the hip replacement procedure.

The measuring bar, when fitted onto the ilium pin top section, forms a right angle to the ilium pin, extends across the acetabulum, and over the proximal femur. The position of the measuring bar relative to the ilium pin is maintained as by turning a set screw lock of the ilium end mount into engagement with ilium pin, locking the measuring bar to the ilium pin top section.

A femoral slide is arranged to slide along the measuring bar, over a scale scribed therealong, and includes a set screw for passing, when turned, through a side of the femoral slide and into engagement with the measuring bar, locking thereto. A femoral pin that is arranged to receive a positioning collar fitted thereon is for passing through an opening formed through the femoral slide, at a right angle to the measuring bar, with a pin lower pointed end to engage a fixed point or location formed on the proximal femur, below the femoral head. The positioning collar is for turning over the femoral pin upper end to where it engages the top of the femoral slide, with a top collar surface for alignment with a mark of a scale scribed along the femoral pin for determining femoral pin end positioning relative to the ilium surface.

In practice, the ilium pin pair of pointed ends are driven into the ilium to where a surface of a cross bar secured between the pointed ends contacts the ilium surface. So arranged, the ilium pin is to serve as a reference for mounting the other components of the measuring device. The ilium pin top end is fitted through the hole formed through the ilium end mount of the measuring bar, the pin and mount forming a right angle to one another. An alignment of the radial line scribed on the ilium pin end top end with a degree marking of the circle scale is used to establish an off-set of the patient's femur medially or laterally to the patient's acetabulum.

The femoral slide is moved along the measuring bar, traveling over the scale scribed thereon, until a pointed end of the femoral pin that extends at a right angle from that femoral slide is directly above a fixed location that has been formed on the proximal femur surface. Thereat, the femoral pin is extended from the femoral slide to where the femoral pin pointed end engages that fixed location as has been marked on the proximal femur. With the ilium mount end of the measuring bar locked to the ilium pin the femoral slide is locked to the measuring bar after the femoral pin has been fitted through the femoral slide to engage the fixed location on the femur, the position of a femoral slide indicator to the measuring bar scale establishes the distance between the ilium pin and the fixed location marked on the femur. This measurement serves as a reference for reproducing or adjusting the patient's leg length. A collar is turned over the femoral pin top end to where it engages a top surface of the femoral slide, with a collar top surface to serve as an indicator for comparison with a marking of a scale scribed along the femoral pin. The marking as the collar top surface aligns with is the distance that the femoral pin pointed end is below the surface of the ilium whereat the ilium pin is driven into. After the measurements are taken, with the femoral slide left locked to the measuring bar and the femoral pin position maintained, the measuring bar is removed from the ilium pin and the pathologic hip is dislocated in a surgical hip replacement procedure. The measurements obtained prior to the dislocation using the invention are then used by the surgeon during the seating of and adjustment to the hip prosthesis in a reproduction of or in an alteration to the patient's leg length and to reproduce the medial or lateral off-set of their femur to the prosthesis acetabulum.

THE DRAWINGS

These and other objects and features of the present invention will become apparent from the following description of a preferred embodiment thereof taken in conjunction with the following drawings in which.

DETAILED DESCRIPTION

Figure 1:
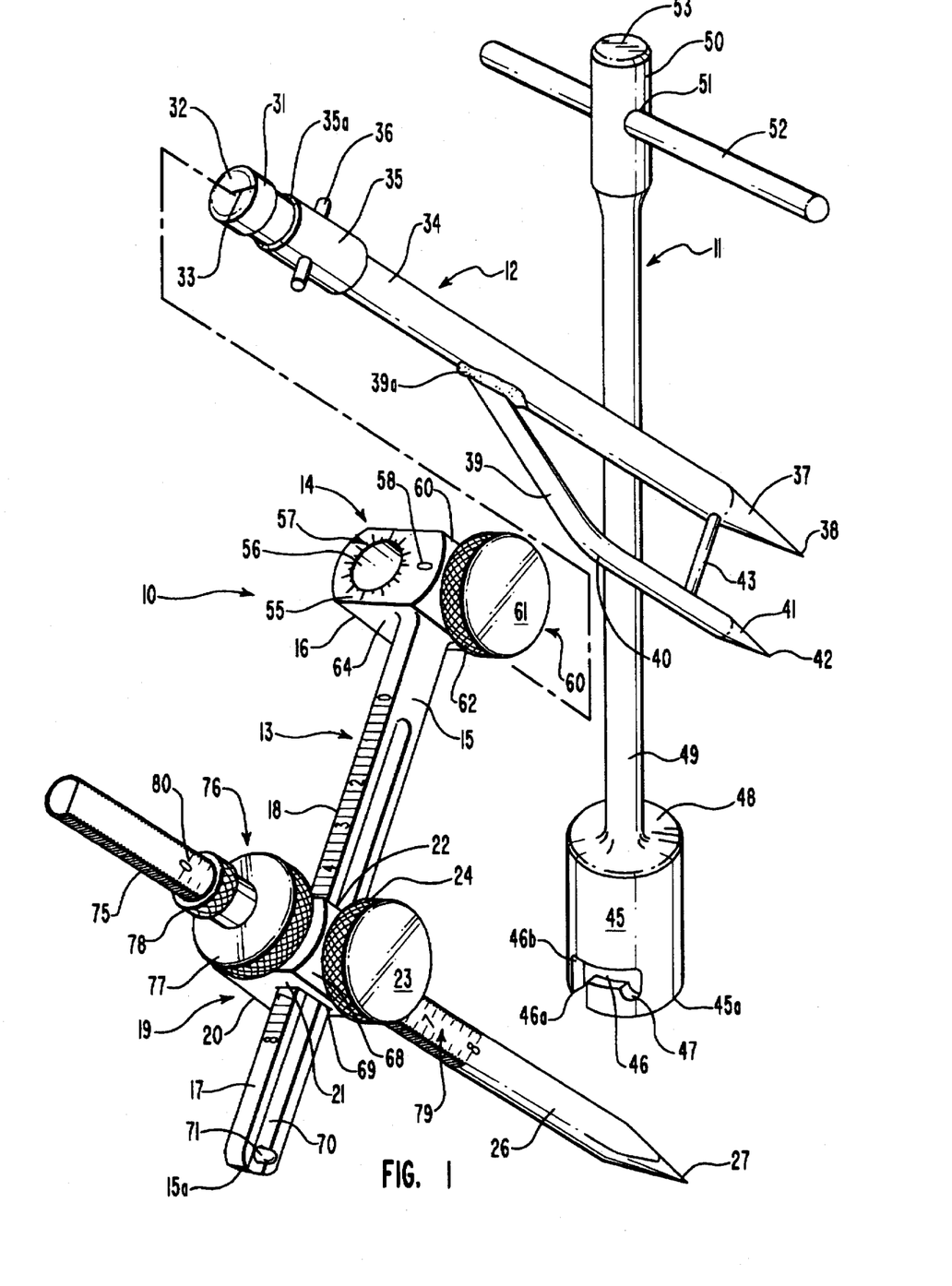
FIG. 1 is a side elevation perspective view of a measuring device of the invention showing an ilium pin with a driver separated therefrom, and with the ilium pin lower end shown as two parallel pointed end pins with a cross bar therebetween, and with an upper or top ilium pin end aligned to receive an ilium pin mount end of a measuring bar fitted thereover, with a femoral slide shown fitted onto the measuring bar to travel therealong over a measuring bar scale, and showing a femoral pin fitted through the femoral slide with a collar turned on the femoral pin to engage a top surface of the femoral slide.
Figure 2:
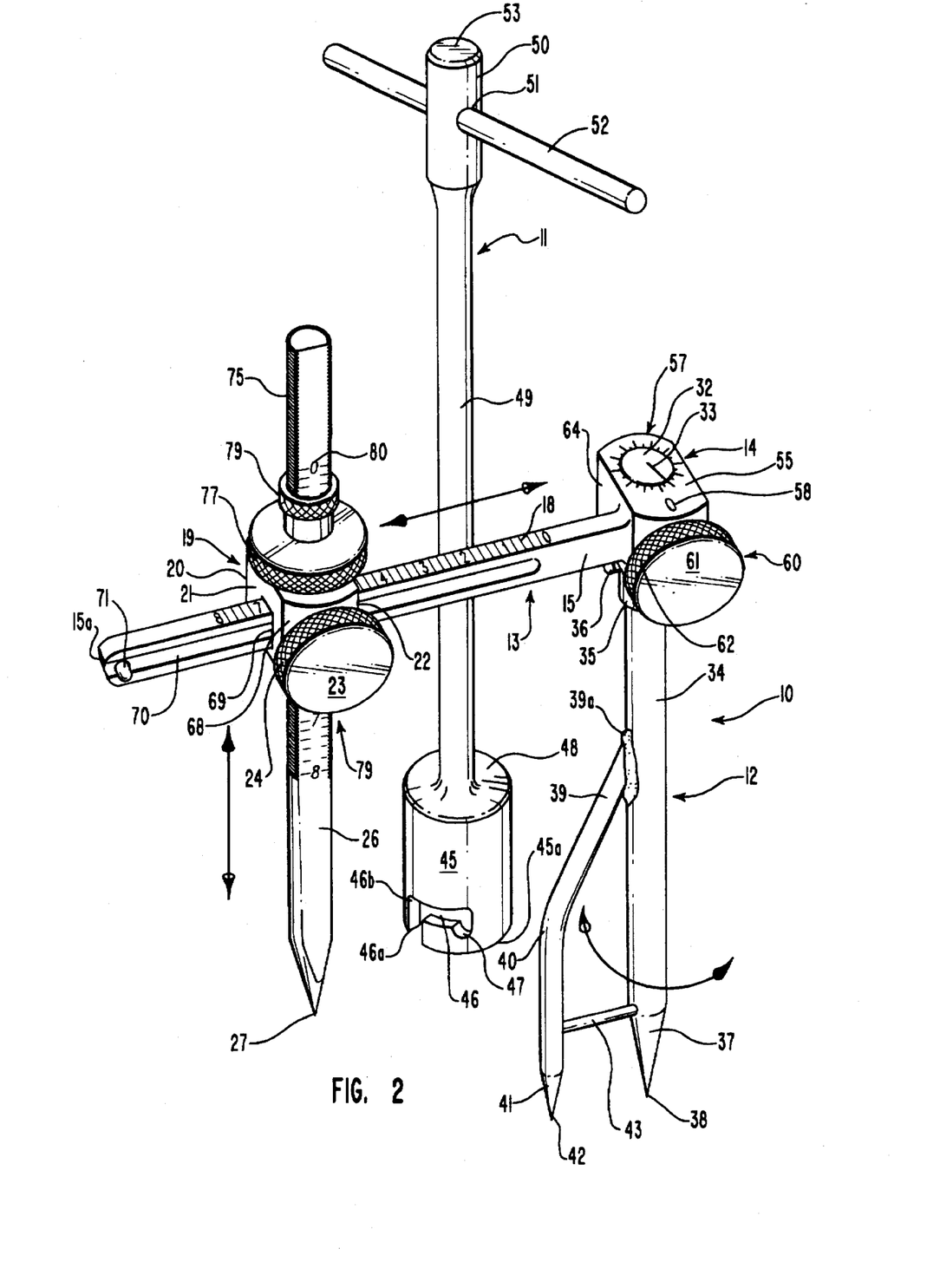
FIG. 2 is a side elevation view of the assembled measuring device of FIG. 1 showing, with a curved arrow, a rotation of the measuring bar ilium end mounting around the ilium pin top end section, showing, with a straight horizontal arrow, femoral slide travel along the measuring bar and showing, with a straight vertical arrow, femoral pin travel through the femoral slide.
Figure 4:
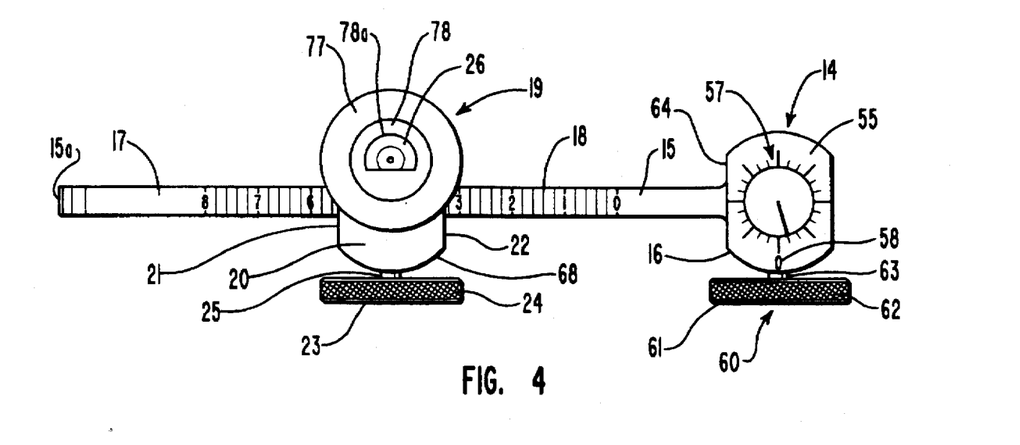
FIG. 4 is a top plan view taken along the line 4—4 of FIG. 3C, showing the measuring bar scale with the femoral slide positioned thereon and showing the ilium pin radial line aligned with a degree marking of the scale scribed around the ilium pin hole that is formed through the ilium pin mount.

The present invention is in a device for measuring leg length and femur off-set medially or laterally to the acetabulum in a total hip replacement procedure, and is hereinafter referred to as measuring device 10. The measuring device 10, as shown in FIGS. 1 and 2, includes a separate driver 11, whose use and function are discussed later herein with respect to installation of an ilium pin 12 in a patient's ilium 30. The measuring device 10, as shown best in FIGS. 1 and 2, includes the ilium pin 12 and a measuring bar 13, that has, as one end thereof, an ilium pin mount 14 that includes a straight longitudinal hole formed therethrough that is for receiving the ilium pin. A measuring bar body 15 of the measuring bar 13 is secured, to extend at a right outwardly from a side of an ilium pin mount body 16. The measuring bar body 15, as shown in FIGS. 1, 2 and 4, is preferably a straight section having a rectangular cross section and includes a scale 18 scribed along a top surface 17. The scale 18, as shown, progresses from a zero (0) marking, adjacent to the ilium pin mount, with equal spaced markings therealong, to a marking identified with an eight (8). The scale 18 is preferably in centimeters though, of course, the scale could be in inches, within the scope of this disclosure.

A femoral slide 19, shown in FIGS. 1, 2 and 3B through 4, is open horizontally to fit onto and to slide along the measuring bar body 15. The femoral slide 19 includes a body 20, shown as a block, having flat rear and front walls 21 and 22, respectively, that are parallel and will each form a right angle to the top surface 17 of the measuring bar body 15 when the slide is installed thereon. Dependant upon the scale 18 layout on the top surface 17, either wall 21 or 22 can serve as a reference for comparison to the markings on scale 18. With the scale 18 spacing from the ilium end mount body 16, as shown, the femoral slide front parallel wall 22 is preferably used to align with a marking on scale 18 for determining the distance between an ilium pin 12 mounted in a patient's ilium 30, and a proximal femur 28 fixed location 28a. This measurement is made prior to a dislocation of the patient's pathologic hip in a total hip replacement surgical procedure and is for use in reproducing or adjusting that leg length in the installation of the hip prosthesis, as shown in FIG. 3C.

The femoral slide 19 travels along the measuring bar fixed to a location above the point 28a on the proximal femur and thereat is preferably locked in place as with set screw arrangement. Such set screw arrangement includes a knob 23, formed as a disk having a toughened outer circular surface 24 to facilitate its being gripped between a surgeon's fingers. The knob 23, when turned, turns a set screw shaft 25, shown in FIG. 4, into a body 20 of the femoral slide 19, passing through the side of body 20 and into the measuring bar opening to engage the side of measuring bar 15. Shown in FIG. 3C, a straight femoral pin 26 is shown fitted to slide through a vertical hole 74 formed through the femoral slide 19 such that a pin pointed end 27 will be moved into engagement with a fixed location 28a, shown as an X, formed on the proximal femur 28, below the femoral head 29, shown also in FIGS. 3A and 3B.

Figure 3A:
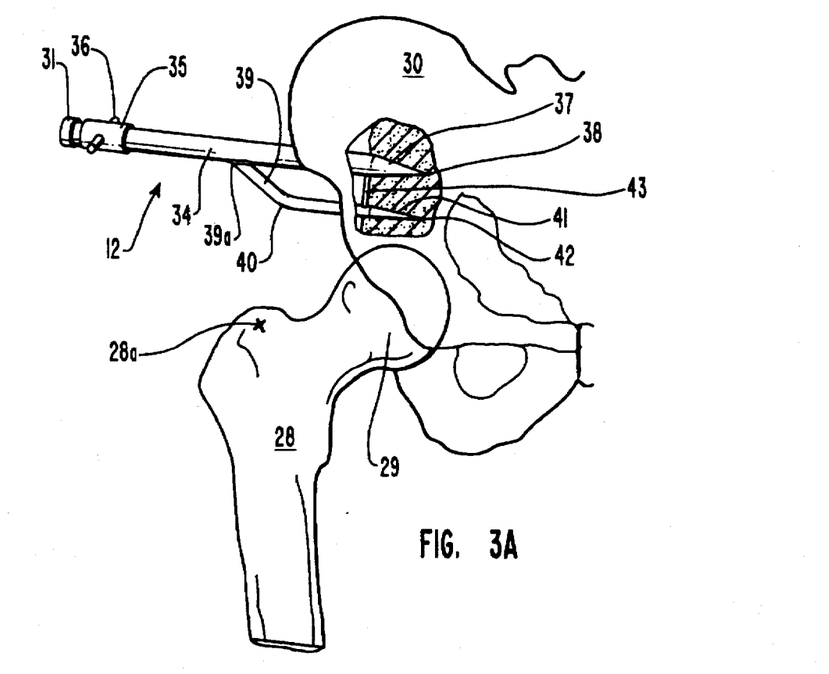
FIG. 3A is a side elevation view of a patient's hip showing the ilium pin lower pointed ends as having been driven into the ilium to where the cross piece engages the ilium surface and showing, with an X scribed thereon, a fixed location on the proximal femur.
Figure 3B:
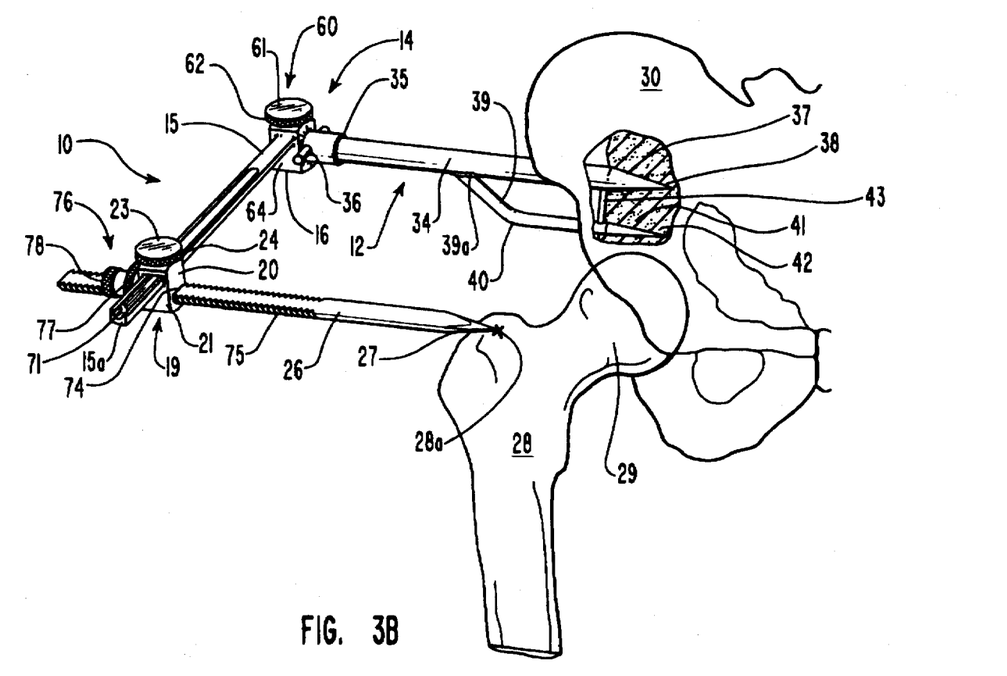
FIG. 3B is a view like that of FIG. 3A additionally showing the measuring bar ilium pin mount as having been fitted over the ilium pin upper end and showing a femoral slide as having traveled along the measuring bar to a location whereat the femoral pin pointed end engages the fixed location.
Figure 3C:
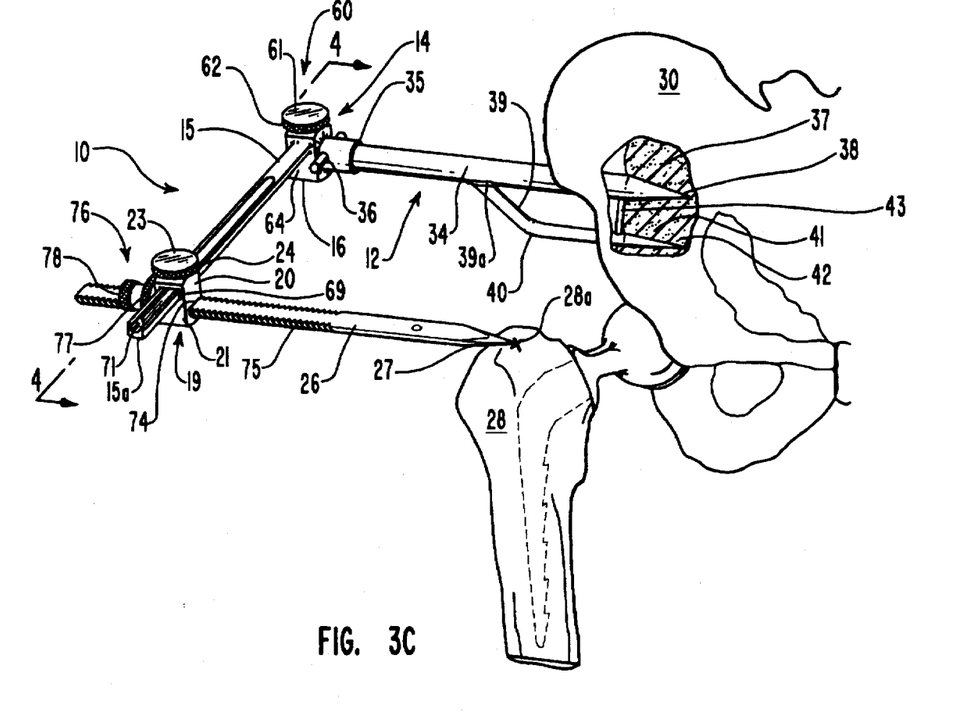
FIG. 3C is a view like that of FIG. 3B only showing the femoral head as having been removed and replaced with a femoral component of a hip prosthesis.

Hereinabove the measuring device 10 is set out to include the ilium pin 12 for mounting in a patient's ilium whereto the measuring bar 13 includes a measuring bar body 15 that connects to extend at a right angle outwardly from side 64 of the ilium mount body 16, with the femoral slide 19 to travel along the measuring bar body 15. The femoral slide 19 is moved along the scale 18 formed along a top surface 17 of measuring bar body 15 to a location whereat the femoral pin 26, when extended from the femoral slide, will contact, with its pointed end 27 of the fixed location 28a on the proximal femur 28. At this position, to determine the distance between the location on the ilium 30 surface wherein the ilium pin 12 is fixed and the location 28a on the proximal femur, as shown best in FIG. 4, a front wall 22 of the femoral slide body 20, along its lower edge, is compared against the scale 18. This measured distance between the ilium pin 12 the and fixed location 28a is reproduced in the installation of the hip prosthesis, as shown in FIG. 3C, or can be used as a reference by a surgeon to alter the patient's leg length during the installation of a hip prosthesis, to correct a chronic problem.

As set out above, the ilium pin 12 is arranged to be driven, as by hammering, into the patient's ilium 30 prior to a pathologic hip dislocation, with the mounted ilium pin to serve as a reference for measuring. Shown in FIG. 1 and in FIG. 5, the ilium pin 12 includes a body 34, shown as a straight rod, that has a round cross section and includes a head end 31 with a top flat face 32. A straight radial line 33 is scribed in the pin top face, from the pin face center to its edge. Adjacent to the head end 31, the ilium pin body 34 is stepped inwardly and receives a collar 35 secured therearound. The collar 35 includes aligned posts 36 that extend from reciprocal points around the circular collar surface with the posts 36 end portions to serve as mounting points for receiving the driver 11 fitted thereto. A collar 35 top edge 35a is to receive and block further travel of the ilium mount 16 as it is slid onto the ilium pin head end 31, as set out below. From collar 35, the ilium pin is a straight section, terminating in a bottom tapered portion 37 that ends in a point 38. At an intermediate location along the pin straight section, a second pin 39 is attached, as by a weld 39a, so as to extend outwardly and is bent inwardly at bend 40. The second pin 39, from bend 40, is parallel to the body 34 and terminates in a tapered portion 41 that ends in a point 42. A transverse bar 43 is shown connected at its ends to extend at right angles, respectively, from the sides of pin 34 and second pin 39. The transverse bar 43, as shown in FIGS. 3A through 3C and in FIG. 5, is for engaging the ilium surface, limiting further penetration of the ilium pin pointed ends 38 and 42 into the patient's ilium 30.

The ilium pin 12 is installed in the patient's ilium 30 to extend from the bone surface at approximately a right angle, and is to receive attach the measuring bar 13 attached thereto. To provide ilium pin 12 installation, as shown in FIGS. 3A through 3C and in FIG. 5, a cylinder end 45 of driver 11 is arranged for fitting onto the ilium pin head end 31. The driver cylinder end 45 is open internally to pass over the ilium pin end and is turned thereon to where an open end 46a of each of a pair of slots 46 comes into alignment with end portions of posts 36 that extend outwardly from opposite sides of the collar 35. With the cylinder end 45 fitted thereover, the posts 36 are to travel up into a vertical section of slot 46 to a right angle bend 46b whereat the driver cylinder end 45 is turned such that the posts 36 end portions travel along horizontal sections of slot 46 to a slot end that has an arcuate cut-out 47 as a bottom slot edge. The arcuate cut-out 47 is to receive the end portions of posts 36, securing the ilium pin 12 top or upper end collar 35 to the driver cylinder end 45. This coupling is useful for facilitating pulling the ilium pin out of the patient's ilium 30 at completion of the hip replacement surgical procedure.

Figure 5:
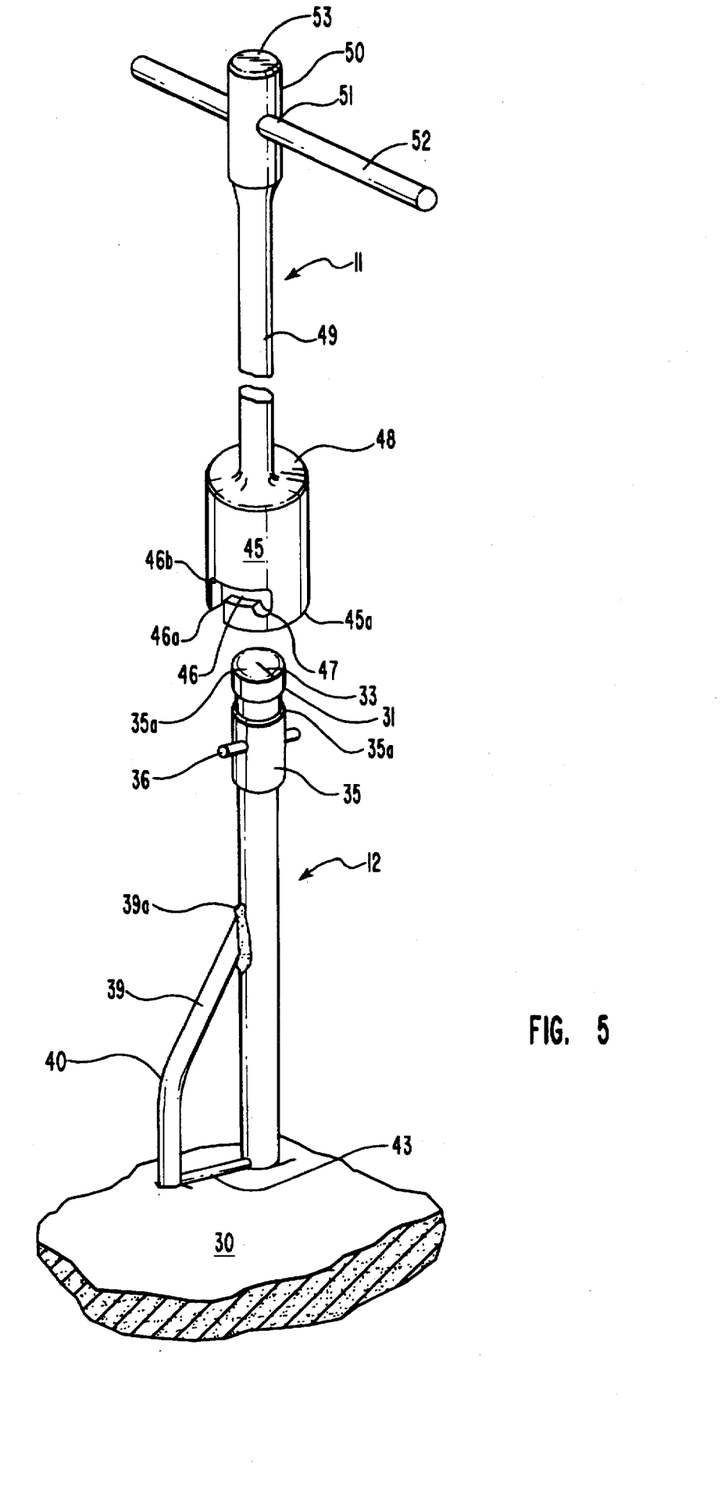
FIG. 5 is a side elevation perspective view showing a section of the ilium wherein the ilium pin parallel pin pointed ends have been driven to where the ilium pin cross bar engages the ilium surface, and with an anvil end of a driver shown exploded off from the ilium pin top end.

Shown in FIGS. 1, 2 and 5, the driver 11 includes a straight rod body 49 that is mounted at a lower end to the center of a flat top surface 48 of the cylinder end 45, extending axially therefrom, and is sloped outwardly into a straight cylindrical top end 50 wherethrough a lateral hole 51 is formed. A straight rod shaped handle 52 is fitted through the lateral hole 51 and is preferably secured therein. The cylindrical top end 50 has a flat top surface 53 that is for striking, as with a hammer, not shown, to drive the ilium pin 12 pointed ends 38 and 42 into a patient's ilium 30, as shown in FIGS. 3A through 3C and 5. To transmit which hammer blows into the ilium pin 12, the driver cylindrical top end 50 and straight rod body 49 are preferably solid, and the cylinder end 45 includes a flat top inner surface against which the flat top 32 of the ilium pin 12 rests to transmit hammer blows into the ilium pin. The handle 52 maintained across the driver cylindrical top end 50 is for gripping by a surgeon, after completion of the replacement procedure, to move the driver 11 and ilium pin 12, connected through the cylinder 45, so as to loosen the ilium pin ends 42 and 38 allowing the ilium pin to be pulled out of the patient's ilium 30.

Preferably, in installing the ilium pin 12, the pin is positioned on the ilium such that an imaginary straight line between the respective pin ends 42 and 38 will be at approximately a right angle to radial line 33 that is formed in the top surface 32 of the ilium pin head end 31. Which radial line 33 is compared against a scale 57, as set out below, to serve as a reference for reproducing leg medial or lateral displacement. To determine leg displacement before dislocation of the pathologic hip, with the measuring bar body 15 ilium mount body 16 installed onto the ilium pin 12, and with the femoral slide 19 moved along the measuring bar body to where the pointed end 27 of the femoral pin 26 that has been extended from the femoral slide body 20 contacts the fixed location 28a on the proximal femur, as shown in FIGS. 3B and 4. Thereat, the radial line 33 on the ilium pin head end 31 will approximately point at a scale marking at or on either side of a zero (0) marking 58 of a full circle scale 57 that has been scribed around an opening 56 formed through the ilium mount body 16. Shown in FIG. 2, the radial line 33 is aligned with a compass marking that is counterclockwise from the zero (0) marking 58, shown herein as approximately a ten (10) degree marking. The scale marking indicates displacement of the leg prior to the procedure, and with FIG. 4 showing this same displacement reproduced in the patient's leg after the procedure.

With the measuring device 10 installed, as described above, and prior to the surgeon performing a dislocation of the pathologic hip, the radial line 33 positioning relative to the a marking of full circle scale 57 is used by the surgeon to reproduce the original positioning of the femur relative to the acetabulum. Generally, this displacement angle is reproduced in the procedure, but should the surgeon visually determine a need to correct femur angular displacement, the original reference line 33 positioning relative to a particular marking on the full circle scale 57 can be used as a reference to calculate a new or substitute angle. Such new or substitute angle is then set into the measuring device 10 by a rotation of the measuring bar 13 to where the radial line 33 points at the selected scale 57 marking, and the is femur adjusted appropriately in the hip replacement procedure.

The measuring bar 13 is removed from its mounting to the ilium pin 12 prior to a dislocation of the pathologic hip. After dislocation, in the performance of the surgical procedure, the femoral head is removed and ultimately replaced with a femoral prosthesis, as illustrated in FIG. 3C and with the acetabulum is replaced with a prosthetic socket. The prosthesis elements are fitted together to check alignment. At this time, the measuring bar 13 is reinstalled onto the ilium pin 12 head end 31 and the positioning of the radial line 33 in relation to a selected marking on the full circle scale 57 is reproduced. This position is maintained by a surgeon manually gripping, between thumb and index finger, a roughened surface 62 of a disk shaped knob 61 end of a set screw type lock 60, as shown in FIGS. 1, 2 3B, 3C, and 4, turning the end of a shaft end of a shaft 63, shown in FIG. 4, into engagement with the ilium pin 12 surface, so as to lock the components together. In which locking, the shaft 63 end engages the side of ilium pin, above the collar 35. So arranged, a top edge 35a of the ilium pin collar 35 engages an undersurface of the ilium mount body 16, around an edge of the hole 56 therethrough, blocking further travel of the ilium mount block 16 along the ilium pin 12, as shown best in FIG. 2.

Shown in FIGS. 1 and 2, the measuring bar 13 body 15 is secured to the ilium mount body 16 so as to extend at a right angle outwardly from a flat wall 64 and, as set out above, includes the scale 18 scribed along the body flat top surface 17. The markings of which scale 18, as shown, are for individual alignment with a lower edge of front wall 22 of the femoral slide 19 for determining the reference distance of the femoral pin 26 from the ilium pin 12. Scale 18 can be in centimeter, inches, or the like. This measured distance is maintained by the set screw lock that, as set out above, is operated by turning the knob 23, to move an end, not shown, of set screw shaft 25 through a side 68 of a set screw body 20 into engagement with the measuring bar 15.

Shown best in FIGS. 1 and 2, for establishing the reference distance, prior to pathologic hip dislocation, the measuring bar body 15 is fitted through a lateral passage 69 formed through the femoral slide body 20 that is shown herein as having a rectangular cross section, with the measuring bar body to travel freely back and forth therein. For maintaining positioning of the femoral slide 19, the measuring bar body 15 includes a straight longitudinal slot 70 formed along a side of the measuring bar body that opens at end 51a. The slot 70, proximate to its open end, includes a stop pin 71 fitted through measuring bar body to extend across the slot. With the femoral slide appropriately located on the measuring bar body 15, and the set screw shaft 25 turned in the femoral slide body 20 to engage the wall of longitudinal slot 70, the femoral side 19 will be locked to the measuring bar body 15. With, however, the set screw shaft 25 end just turned into the slot 70, when the femoral slide body 20 is slid along the measuring bar body 15 to the slot 70 open end, the set screw shaft 25 end will engage the stop pin 71, prohibiting travel of the slide body 20 off of the measuring bar body 15.

As set earlier herein, the femoral pin 26 is fitted to slide laterally through the femoral slide body 20 to where its pointed end 27 contacts the femoral fixed location 28a. To allow femoral pin 26 travel, the femoral slide body 20 includes a straight longitudinal passage 74 formed therethrough that passes through both the slide bottom body surfaces and, as shown in FIGS. 3B and 3C, preferably has a half moon cross section. The half moon cross sectional configuration of passage 74 is to accommodate the femoral pin 26 that preferably also has half moon cross section, as shown best in FIG. 4.

The femoral pin 27 is shown in FIGS. 1, 2, 3B and 3C, as threaded at 75 from its top end to its mid section to receive a top hat shaped collar 76 turned thereover. The longitudinal passage 74 formed through the femoral slide body is preferably smooth walled to allow the femoral pin to slide freely therethrough. So arranged, the femoral slide 19 is moved appropriately along the measuring bar 13, to a location where the surgeon urges the femoral pin 26 out of the longitudinal passage 74 such that the femoral pin pointed end 27 contacts the femoral location 28a. Thereat, the femoral slide body 20 is locked, as set out above, to the measuring bar body 15 by turning the set screw knob 23. The femoral pin 26 pointed end 27, in most, if not all, procedures, will be a distance above where the ilium pin 12 horizontal bar 43 rests on the ilium surface, as shown in FIGS. 3A through 3C and FIG. 5. For establishing the femoral pin pointed end 27 distance above the ilium surface, prior to dislocation of the pathologic hip in the hip replacement procedure, a scale 79 is scribed along the femoral pin 26, that is shown in centimeters but could be in inches, or the like. The scale 79, as shown, starts at a zero (0) location 80 that is apart from and is spaced downwardly from the femoral pin top end, terminating in a marking, shown as eight (8), located at a midsection of the femoral pin.

With the femoral pin 26 pointed end 27 positioned on the femoral location 28a, as shown in FIGS. 3B and 3C, the top hat shaped collar 76, that includes a disk 77 maintaining a sleeve 78 axially mounted thereto, is turned onto the femoral pin threads 75, to travel therealong to where the disk bottom face contacts the top of the femoral slide 19. Thereat, a top face of sleeve 78 will align with a particular scale marking on scale 79. This scale marking is the distance that the fixed location 28a on the femur is below the ilium 30 surface at the ilium pin 12 cross bar 43 and is used by the surgeon as a reference for femur positioning during the hip replacement surgical procedure. To maintain top hat shaped collar 76 positioning, a threaded center longitudinal passage 78a is formed therethrough, shown in FIG. 4, that is turned onto the threads 75 formed along the femoral pin 26 surface. The distance measurement as determined by an alignment of the top face of sleeve 78 to a marking on scale 79 can either be reproduced in the hip replacement procedure or can be used as a basis for making leg adjustments thereto, as determined by the surgeon, in that hip replacement procedure. Such adjustments are provided by a selection of a particular size of hip prosthesis for use in the procedure, the preparation of the proximal femur and a fitting of the prosthesis femoral component thereto, as shown in FIG. 3C, that includes a preparation of the proximal femur intramedular channel, and by a selection and mounting of the prosthesis acetabular component, along with appropriate adjustments to ligament tensioning as are made in the reattachment of the hip ligaments and muscles across the joint.

While a preferred embodiment of my invention in a device for measuring leg length and hip off-set during a total hip replacement procedure has been shown and described herein, it should be understood that the present disclosure is made by way of example only and that the invention may be utilized other than as described without departing from the subject matter coming within the scope of the following claims, and a reasonable equivalency thereof, which claims I regard as my invention.

I claim:

1. A device for use in an orthopedic surgical procedure for a replacement of a patient's hip for measuring the length of the patient's leg and displacement prior to dislocation of the pathologic hip comprising, an ilium pin to be driven into a patient's ilium, an indicator means formed on said ilium pin that further includes an upper section for mounting an ilium pin mount of a measuring bar; a measuring bar with a straight member having scale markings scribed therealong, with an ilium pin mount formed in one end and including an angular measuring means for determining a relative position of said ilium pin to said ilium pin mount for determining angular displacement; a femoral slide arranged for travel along said measuring bar straight member; a femoral pin means for extension at a right angle from said femoral slide and having an end for positioning on a location on the patient's proximal femur; and means on said femoral slide for comparison with said measuring bar scale markings for determining distance of said femoral slide from said measuring bar ilium pin mount.

2. A device as recited in claim 1, wherein the ilium pin includes a pair of first and second pin portions, said first pin portion being a straight lower end of said ilium pin and said second pin portion connecting, at its upper end, to a mid section of said ilium pin so as to be at an angle therefrom with, at a midsection thereof, said second pin portion bent back towards, to be essentially parallel to, said first pin portion, and said first and second pin portions each have aligned pointed ends; and a straight bar is secured at its ends between and at right angles to said first and second pin portions and is spaced apart from their aligned pointed ends.

3. A device as recited in claim 1, wherein the ilium pin upper section that receives the measuring bar ilium pin mount includes a collar secured therearound, apart from the ilium pin upper end, which said collar is to seat said ilium pin mount whereby an ilium pin upper end surface will approximately align with a top surface of said ilium mount; and said angular measuring means is a radial line scribed on a top end surface of said ilium pin and will align with a marking of a full circle scale formed around the opening formed through said ilium pin mount wherethrough said ilium pin is fitted.

4. A device as recited in claim 3, further including a driver means for use in installing and withdrawing the ilium pin into and from a patient's ilium to include a straight shaft having a top end arranged to receive a force applied thereto, and includes a sleeve secured across the shaft bottom end that provides a means for coupling said sleeve to said ilium pin upper end consisting of at least one slot formed in said sleeve that opens to a lower sleeve edge and extends vertically therefrom into the sleeve as a first section whereat the slot translates to a horizontal second section; and the collar further includes at least one pin means extending outwardly therefrom that is for fitting into said sleeve slot opening and to pass therealong.

5. A device as recited in claim 1, further including means for releasably locking together the measuring bar ilium pin mount and ilium pin.

6. A device as recited in claim 1, wherein the measuring bar straight member has a rectangular cross section, and includes the scale scribed along a top surface thereof; and the means for comparison is a face of the femoral slide that is at approximately a right angle to the scale.

7. A device as recited in claim 1, further including means for releasably locking the femoral slide to the measuring bar straight member.

8. A device as recited in claim 7, further including a longitudinal slot formed into the surface of a side of the measuring bar, the releasable locking means is a set screw having a threaded shaft for turning through a threaded hole formed through the femoral slide, whereby, with said femoral slide fitted onto said measuring bar straight member, an inner end of said set screw shaft will align with to travel into said longitudinal slot, which said threaded shaft includes a head formed across its outer end; and stop means for arrangement within said longitudinal slot for blocking, by contact with said set screw shaft inner end, travel of said femoral slide off of said measuring bar.

9. A device as recited in claim 1, wherein the femoral pin means is a straight shaft arranged for sliding through a hole formed through the femoral slide and has a point formed in a bottom end, with scale markings scribed therealong from adjacent to femoral pin top end to a femoral pin midsection; and including indicator means for comparison with said scale markings for determining a distance said femoral pin pointed end extends from said femoral slide.

10. A device as recited in claim 9, wherein the femoral pin indicator means is a top surface of a sleeve that is arranged for fitting over to travel along the femoral pin top end portion to where it engages a top surface of the femoral slide, with said sleeve top surface to align with a marking of the scale for indicating distance.

11. A device as recited in claim 10, wherein the femoral pin is threaded from the top end to a mid portion, and the sleeve is internally threaded for turning onto said femoral pin threads.

* * * * *